United States Patent [19]

Chiang et al.

[11] Patent Number: 5,234,690
[45] Date of Patent: Aug. 10, 1993

[54] TRANSDERMAL DRUG DELIVERY DEVICE USING AN UNFILLED MICROPOROUS MEMBRANE TO ACHIEVE DELAYED ONSET

[75] Inventors: Chia-Ming Chiang, Foster City, Calif.; Kenneth J. Colley, Washington, D.C.; Gary W. Cleary, San Mateo, Calif.

[73] Assignee: Cygnus Therapeutic Systems, Redwood City, Calif.

[21] Appl. No.: 749,431

[22] Filed: Aug. 23, 1991

[51] Int. Cl.⁵ ............................................. A61F 13/02
[52] U.S. Cl. ..................................... 424/448; 424/443; 424/447; 424/449
[58] Field of Search ............... 424/448, 449, 443, 447

[56]  References Cited

U.S. PATENT DOCUMENTS

| | | | |
|---|---|---|---|
| 3,598,122 | 8/1971 | Zaffaroni | 424/449 |
| 3,598,123 | 8/1971 | Zaffaroni | 424/449 |
| 3,742,951 | 7/1973 | Zaffaroni et al. | 424/449 |
| 3,797,494 | 3/1974 | Zaffaroni | 424/448 |
| 4,286,592 | 9/1981 | Chandrasekaran | 424/449 |
| 4,533,540 | 8/1985 | Blank | 424/486 |
| 4,559,222 | 12/1985 | Enscore et al. | 424/486 |
| 4,618,699 | 10/1986 | Fialla | 560/86 |
| 4,654,209 | 3/1987 | Leslie et al. | 424/78.25 |
| 4,655,766 | 4/1987 | Theeuwes et al. | 604/891.1 |
| 4,661,441 | 4/1987 | Kajiwara et al. | 430/555 |
| 4,681,584 | 7/1987 | Gale et al. | 424/449 |
| 4,751,087 | 6/1988 | Wick | 424/449 |
| 4,776,850 | 10/1988 | Guse et al. | 604/304 |
| 4,778,678 | 10/1988 | Guse et al. | 424/487 |
| 4,784,857 | 11/1988 | Berry et al. | 424/449 |
| 4,786,282 | 11/1988 | Wagle et al. | 604/307 |
| 4,956,181 | 9/1990 | Bayer et al. | 424/448 |

Primary Examiner—Thurman K. Page
Assistant Examiner—Leon R. Horne
Attorney, Agent, or Firm—Morrison & Foerster

[57] ABSTRACT

A delayed onset transdermal drug delivery device exhibiting a delay period of at least six hours comprising a laminated composite of (1) a top backing layer; (2) a pressure rupturable layer underlying (1); (3) a reservoir of a solution of drug in a liquid vehicle between (1) and (2); (4) a wick layer underlying (2) for dispersing the drug once (2) is ruptured; (5) a first adhesive layer underlying (4) that is permeable to the drug; (6) a microporous membrane underlying (5) which is itself impermeable to the drug and whose pores are substantially unfilled prior to application of the device to the skin; and (7) a second adhesive layer underlying (6) that is permeable to the drug but is immiscible in the polymer filling the pores of (6).

13 Claims, 2 Drawing Sheets

TRANSDERMAL DRUG DELIVERY DEVICE USING AN UNFILLED MICROPOROUS MEMBRANE TO ACHIEVE DELAYED ONSET

TECHNICAL FIELD

This invention is in the general field of transdermal drug delivery and relates specifically to devices from which drug is released in a delayed pattern from the time the device is placed on the skin. Devices that release drug in such a pattern are commonly referred to as "delayed onset" devices.

BACKGROUND

Earnest efforts to develop transdermal drug delivery devices that provide drug to the patient in a controlled pattern began in the late 1960s and early 1970s. The principal pattern of delivery that was investigated was substantially constant rate delivery in which delivery began at or shortly after the device was applied to the skin, rose to a desired level, and stayed at that level for a sustained time period. These efforts resulted in numerous patents being issued for devices of various structures that achieved or closely mimicked constant rate delivery. See, for instance, U.S. Pat. Nos. 3,598,122; 3,598,123; 3,797,494; and 4,286,592.

Nitroglycerin (NTG) is among the many drugs that has been administered transdermally. Among the U.S. patents describing transdermal NTG delivery are U.S. Pat. Nos. 3,742,951; 4,533,540; 4,559,222; 4,618,699; 4,681,584; 4,654,209; 4,655,766; 4,661,441; 4,751,087; 4,776,850;, 4,778,678; 4,784,857; and 4,786,282. None of these patents concern delayed onset nitroglycerin delivery. Further, the initial commercial transdermal NTG devices (the Transderm-Nitro and Nitro-Dur devices) are continuous rather than delayed-onset delivery devices.

In the mid-1980s a number of clinical studies raised questions about the efficacy of NTG therapy provided by the then available commercial transdermal devices that administered NTG in a continuous pattern. Specifically, continuous administration was tending to cause tolerance and hemodynamic attenuation This led clinicians to conclude that the ideal regimen for administering NTG would include an overnight "washout period" during which no NTG was administered. Correlatively, it led developers of transdermal devices to propose delayed onset devices for administering NTG.

U.S. Pat. Nos. 4,956,181 describes a delayed onset device for administering NTG. Its device consists of a backing layer, a rupturable pod sandwiched between the backing and a nonwoven fabric layer, a barrier membrane, an adhesive layer, and a release liner. The rupturable pod contains NTG and an activator liquid that is capable of plasticizing the barrier membrane and increasing its permeability to NTG. Once the pod is ruptured, drug and activator migrate down through the barrier membrane, with the activator causing the membrane to become increasingly permeable to the drug. While this patent indicates that an effective delay of up to 12 hr may be achieved, the examples of the patent describe devices that achieve only a 4-6 hr delay.

An object of the present invention is to provide a delayed onset device for administering NTG that provides at least a six and preferably an eight hour delay in administration. The device of the invention does not use plasticization of a barrier membrane as a delay mechanism.

DISCLOSURE OF THE INVENTION

This invention is a device for administering a drug transdermally following application of the device to a subject's skin wherein the delivery of drug is delayed at least about six hours after said application comprising in combinations: (a) a nonrupturable backing layer forming the top surface of the device; (b) a pressure rupturable reservoir underlying (a) and containing the drug dissolved in a liquid vehicle; (c) a wick layer underlying (b) for dispersing the drug once the reservoir is ruptured; (d) a layer of a drug permeable polymer underlying (c); (e) a microporous membrane underlying (d) and whose pores are substantially unfilled prior to application of the device to the patient's skin; (f) a layer of a drug permeable adhesive polymer underlying (e) and forming the basal layer of the device; wherein it initially takes at least about six hours for the drug to diffuse to the skin from the reservoir once the reservoir is ruptured and the device is applied to the skin.

MODES OF CARRYING OUT THE INVENTION

Figure 1:
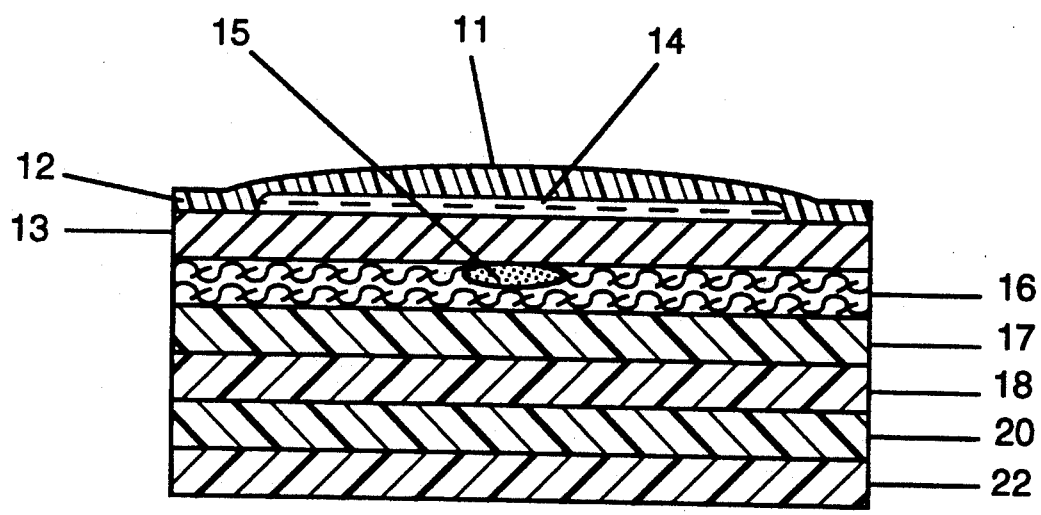
FIG. 1 is a sectional view of an embodiment of the invention for administering NTG. The drawing is not to scale. The thicknesses of the layers of the embodiment are exaggerated for the purposes of illustration.

The drawing shows a preferred embodiment, generally designated 11, of the delayed onset device of the invention. The top surface of the device is defined by backing layer 12. It is made of a material or combination of materials that is substantially impermeable to the solution of NTG in the liquid vehicle, does not absorb significant amounts of the NTG solution, and is capable of being sealingly bonded (e.g., by heat sealing or crimping) at its periphery to the underlying microporous membrane layer 18 (described below). In addition, the mechanical properties of the backing should be such that it does not rupture coincident with the rupture of the underlying rupturable layer 13. It is also preferably flexible and/or elastomeric. Examples of materials from which the backing layer may be formed are elastomeric polymers such as polyether block amide copolymers (e.g., PEBAX copolymers), polyethylene methyl methacrylate block copolymers, (e.g., NUKRELL polymers), polyurethanes (e.g., PELLATHANE polymers), silicone elastomers, polyester block copolymers such as HYTREL, rubber-based polyisobutylene, styrene, and styrenebutadiene and styrene-isoprene copolymers. Flexible polymers include polyethylene, polypropylene, and polyesters such as polyester terephthalate (PET), which may be provided as films or laminates. The thickness of the backing layer will normally be in the range of 0.01 to 0.15 mm, more normally 0.02 to 0.1 mm. The backing may optionally be pigmented (e.g., to resemble skin color).

Backing layer 12 has a cavity that serves as a reservoir or container for a liquid formulation of NTG, generally designated 14. Formulation 14 comprises NTG in a liquid vehicle. Examples of suitable liquid carriers are lower alkanols such as methanol, ethanol, isopropanol, glycols such as propylene glycol, and the like. Propylene glycol is preferred. The formulation may also contain additional ingredients such as a dye which may serve as an indicator of rupture of the reservoir. The NTG will normally comprise 2 to 20% by weight of the formulation, more normally 5 to 10% by weight. The total amount of NTG in the reservoir will normally be 50 to 300 mg, more normally 100 to 150 mg.

Directly underlying the cavity and backing layer is a pressure-rupturable layer 13. Layer 13 is sealed to the overlying backing layer 12 (and underlying layers to the microporous membrane layer 18) about the periphery of the cavity containing the NTG formulation 14. Layer 13 is also impermeable to the NTG formulation and serves as the basal wall of the reservoir. It is made of a material that may be ruptured with normal finger pressure such as aluminum foil coated with a heat sealable layer of ethylene vinyl acetate copolymer, polypropylene or polyethylene. Underlying layer 13 in registry with the reservoir is a hard, solid (incompressible) body 15 to which finger pressure may be applied to facilitate the rupture or tearing of layer 13 below the reservoir to release the liquid formulation of NTG from the reservoir. The body is smaller in dimension than the cavity containing the NTG solution. It will typically be made from hard materials such as polycarbonate, polypropylene.

Immediately below the rupturable layer 13 is a wick layer 16 that is capable of dispersing or spreading the liquid formulation of NTG transversely (parallel) to the basal surface of the device. The wick layer does not absorb or retain any substantial amount of the NTG formulation and functions merely to spread the formulation across the device. It is not a barrier to diffusion of the NTG from the reservoir to the skin surface. The wick layer is preferably made from a nonwoven polymeric fabric such as spun-bonded polyester. It will normally have a basis weight of 0.2 to 1 oz./yard$^2$, preferably 0.4 to 0.6 oz./yard$^2$. The wick layer must be capable of adhering to the adjoining layers of the device under conditions of use (i.e., in the presence of adsorbed NTG formulation) and be sealable (e.g., by heat) to the overlying layers and to the underlying microporous membrane.

Underlying the wick layer 16 is a first layer of a polymer layer 17 that is permeable to the NTG formulation. The diffusion coefficient of NTG in this layer will normally be $1 \times 10^{-7}$ to $1 \times 10^{-8}$ cm/sec. Its thickness will normally be 0.02 to 0.3 mm, more usually 0.02 to 0.15 mm.

The next layer is a microporous membrane layer 18. The material from which the membrane itself is made is substantially impermeable to the NTG formulation and to the adhesive of layers 17 and underlying adhesive layer 20. Examples of microporous materials are microporous polypropylene (CELGARD, Hoechst-Celanese), microporous polyethylene (COTRAN,3M), and microporous polytetrafluoroethylene (TEFLON, Gortex). The membrane will typically have a pore volume in the range of 10% to 60%. The pores are unfilled prior to application of the device to the skin. These voids delay the time it takes for the drug to migrate from the reservoir to the skin. The thickness of the microporous membrane layer will normally be 0.001 to 0.1 mm.

As indicated, a second adhesive layer 20 underlies the microporous membrane. The second adhesive layer may have the same or different composition as the first layer. The thickness of the second adhesive layer will normally be 0.02 to 0.3 mm, more usually 0.02 to 0.15 mm. Examples of adhesives from which the adhesive layers 17 and 20 may be made are polysiloxanes, polyacrylates, polyurethanes, and ethylene-vinyl acetate copolymers.

A standard release liner layer 22 underlies the second adhesive layer.

The delayed onset devices of the present invention are designed to be worn for a one-day period and then replaced. In the case of NTG, the devices will normally be placed on the skin shortly before the individual goes to sleep at night. Thus, the period during which the wearer receives insignificant NTG will coincide roughly with the wearer's waking hours. This pattern of delivery provides NTG when most needed—upon awakening and through the day—and allows the level of NTG in the wearer's circulation to wash out or decline during sleep so that tolerance to NTG is lessened.

In use, the device is removed from its packaging and gripped such that a force may be applied from the basal surface against the solid body 15 to cause the solid body to penetrate and rupture layer 13. The release liner layer is then removed and the device is placed on the skin with the basal layer of the second adhesive layer 20 in drug-delivery contact with the skin surface. The rupturing of layer 13 permits the liquid NTG formulation 14 to be released onto the wick layer 16. The adsorbent properties of the wick layer cause the liquid to be dispersed across (parallel to the basal surface) the device. The liquid then diffuses through the first adhesive layer, the pores of the microporous membrane layer, and the second adhesive layer. The NTG is released from the basal surface of the second adhesive layer into the skin. The extent of the delayed onset will depend upon the diffusion coefficients of the polymers formed the first and second adhesive layers, the thicknesses of those two layers, the porosity characteristics of the microporous membrane, and the thickness of the microporous membrane. With the ranges of these parameters given above a delay of at least eight hours is achieved before skin flux of NTG reaches about 2 $\mu g/cm^2/hr$. During the delay period the NTG skin flux ranges between 0 and about 2 $\mu g/cm^2/hr$. After the delay period the skin flux rises steadily over the remainder of the 24-hour wearing period to a skin flux level of about 5 to 20 $\mu g/cm^2/hr$. These levels of skin flux are as measured by the in vitro diffusion; all studies described in the Examples, infra. The drug delivery area of the device (i.e., the basal surface) is normally in the range of 5–40 cm$^2$, preferably 10–30 cm$^2$.

The devices of the invention may be made by conventional lamination techniques. By way of example, a cavity of desired size is formed in a backing layer. The cavity is filled with a 10% solution of NTG in propylene glycol. The rupturable foil layer is then placed over the cavity. Two sheets of release liner are then coated on one side with adhesive to the desired thickness. One of these sheets is laminated to the wick layer and the release liner is removed. A microporous membrane is then laminated to the exposed side of the adhesive layer and the other adhesive-release liner subassembly is laminated to the other side of the microporous membrane. Care should be taken to apply the device to the skin before the adhesive migrates into the pores of the microporous membrane. Such migration may shorten the period of delay. Finally the backing-NTG reservoir, rupturable layer subassembly is laminated to the wick layer onto which a 1 cm diameter, 2 mm thick disc of polycarbonate has been placed and the assembly is heat-sealed about the periphery of the cavity, thereby heat-sealing the backing through to the microporous membrane layer.

The following examples further describe the invention. These examples are not intended to limit the invention in any manner.

EXAMPLE 1

Water-based acrylic adhesive (Flexcryl 1625, 69% solids) was coated onto a 0.003" thick siliconized polyester release liner film at a thickness of 0.005". The adhesive coating was cured at 70° C. for 30 min in order to remove water; cured thickness was 0.002" (5 mg/cm$^2$). Two such films were prepared.

One of the two adhesive coated release liner films was laminated to a polyester nonwoven (Reemay 2250). The release liner was removed and an unfilled microporous membrane (CELGARD 2400 from Hoescht-Celanese) was laminated to this exposed surface such that the coated side faced the nonwoven. The other side was laminated to the second adhesive film. A disc of this multilaminate was die-cut and laminated to the stratum corneum side of a disc of human cadaver epidermis, using the second adhesive.

A disc of the skin/multilaminate composite was mounted on a glass diffusion cell (effective flux area 0.71 cm$^2$) with the skin side facing the receptor compartment. The donor was 37 μl of a 10% nitroglycerin solution in propylene glycol (SDM 27 from ICI Americas). This solution was placed in the donor compartment directly in contact with the nonwoven. The donor compartment was then occluded, and the cell maintained at 32° C. Samples of the receiving solution were taken periodically and analyzed by HPLC to determine the amount of nitroglycerin permeated in unit time. The experiment was repeated exactly, substituting Nitro-Dur, a commercially available transdermal device, for the multilaminate layer and nitroglycerin vehicle.

Figure 2:
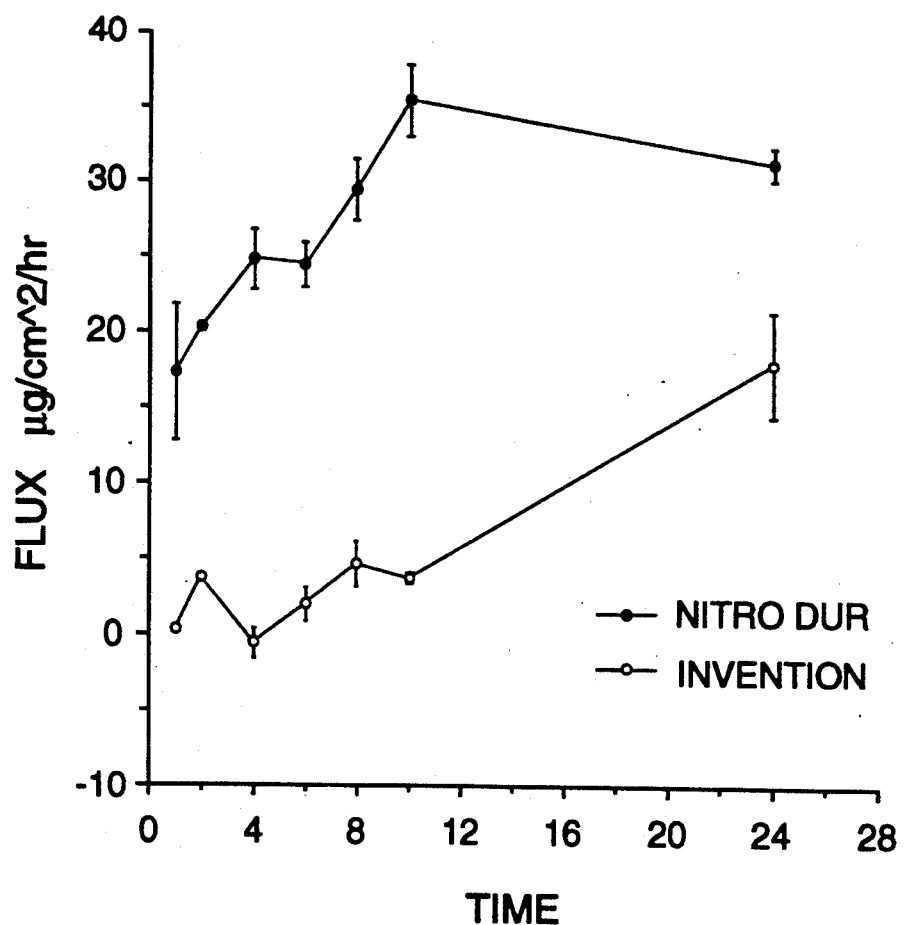
FIG. 2 is a graph of the results of the tests described in Example 1.

As shown in FIG. 2, Nitro-Dur reached substantial flux in 2–4 hr after administration, whereas the composite of the invention delayed full onset to 8 hr after administration.

While the invention has been exemplified in terms of an embodiment for administering NTG, it may also be used to administer other drugs in a delayed onset regimen. Drugs which may be advantageously administered in such a regimen include other vasodilators, analgesics, contraceptives, appetite suppressants, growth factors, and the like. Other modifications of the above-described modes for carrying out the invention that are obvious to those of skill in the fields of transdermal drug delivery device design, materials science, polymer chemistry and related fields are intended to be within the scope of the following claims.

We claim:

1. A device for administering a drug transdermally following application of the device to a subject's skin wherein the delivery of drug is delayed at least about six hours after said application comprising in combination:
   (a) a nonrupturable backing layer forming the top surface of the device;
   (b) a pressure rupturable reservoir underlying (a) and containing the drug in fluid form;
   (c) a wick layer underlying (b) for dispersing the drug once the reservoir is ruptured;
   (d) a layer of a drug permeable polymer underlying (c);
   (e) a microporous membrane underlying (d) made of polymer material that is impermeable to the drug, and is not plasticized, dissolved, or degraded by the contents of the reservoir, and whose pores are substantially unfilled prior to application of the device to the patient's skin; and
   (f) a layer of a drug permeable adhesive polymer underlying (e) and forming the basal layer of the device;
   wherein said delay corresponds to the time it takes the drug to migrate from the ruptured reservoir through said pores to the skin.

2. The device of claim 1 wherein the reservoir is defined by a cavity formed between the backing layer and a pressure rupturable layer overlying the wick layer.

3. The device of claim 2 including means for transmitting manually applied pressure to the pressure rupturable layer.

4. The device of claim 3 wherein the means is an incompresible body underlying the pressure rupturable layer.

5. The device of claim 4 wherein the pressure rupturable layer is a metal foil layer.

6. A delayed onset device for administering nitroglycerin to a subject's skin wherein the delivery of nitroglycerin is delayed at least about six hours after the device is applied to said skin comprising in combination:
   (a) a nonrupturable backing layer forming the top surface of the device;
   (b) a pressure rupturable reservoir underlying (a) and containing a solution of nitroglycerin in propylene glycol;
   (c) a wick layer underlying (b) for dispersing the nitroglycerin once the reservoir is ruptured;
   (d) a first layer of a nitroglycerin permeable adhesive polymer underlying (c);
   (e) a microporous membrane underlying (d) that is made from a polymer material that is impermeable to the solution of nitroglycerin and is not plasticized, dissolved or degraded by the contents of the reservoir, and whose pores are substantially unfilled prior to application of the device to the patient's skin; and
   (f) a second layer of a drug permeable adhesive polymer underlying (e) and forming the basal surface of the device, wherein said delay corresponds to the time it takes the drug to migrate from the ruptured reservoir through said pores to the skin.

7. The device of claim 6 wherein the diffusion coefficient of nitroglycerin in the adhesive polymers of (d) and (f) are $1 \times 10^{-7}$ cm/sec to $1 \times 10^{-8}$ cm/sec.

8. The device of claim 7 wherein the adhesive polymer is an acrylic polymer.

9. The device of claim 6 wherein the skin flux during said at least about six hours is less than 2 μg/cm$^2$/hr and thereafter rises to about 5 to 20 μg/cm$^2$/hr.

10. The device of claim 6 wherein the reservoir is defined by a cavity formed between the backing layer and a pressure rupturable layer overlying the wick layer.

11. The device of claim 10 including means for transmitting manually applied pressure to the pressure rupturable layer.

12. The device of claim 11 wherein the means is an incompressible body underlying the pressure rupturable layer.

13. The device of claim 8 wherein the skin flux during said at least about six hours is less than 1 μg/cm$^2$/hr and thereafter rises to about 5 to 20 μg/cm$^2$/hr.

* * * * *